United States Patent [19]

Schaaf

[11] 3,989,736

[45] Nov. 2, 1976

[54] PROSTAGLANDIN 5-INDANYL ESTERS

[75] Inventor: Thomas K. Schaaf, Old Lyme, Conn.

[73] Assignee: Pfizer Inc., New York, N.Y.

[22] Filed: May 17, 1974

[21] Appl. No.: 471,032

Related U.S. Application Data

[63] Continuation-in-part of Ser. No. 321,664, Jan. 8, 1973, abandoned.

[52] U.S. Cl. .................. 260/468 D; 260/240 R; 260/345.8; 424/305
[51] Int. Cl.² ................................. C07C 177/60
[58] Field of Search .............................. 260/468 D

[56] References Cited
UNITED STATES PATENTS 3,258,542 9/1973 Schneuler ..................... 260/448.8

3,775,462 11/1973 Axen ................................. 260/468

FOREIGN PATENTS OR APPLICATIONS 2,155,546 3/1972 Germany ........................ 260/468

Primary Examiner—Robert Gerstl
Attorney, Agent, or Firm—Connolly and Hutz

[57] ABSTRACT

The prostaglandin 5-indanyl esters and various intermediates employed in their preparation. The novel prostaglandins of this invention have been found to have activity profiles comparable to the parent prostaglandins, but exhibit a longer duration of action than the parent prostaglandins.

7 Claims, No Drawings

PROSTAGLANDIN 5-INDANYL ESTERS

CROSS REFERENCE TO RELATED APPLICATIONS

This application is a continuation-in-part of my copending application, Ser. No. 321,664, filed Jan. 8, 1973 now abandoned.

BACKGROUND OF THE INVENTION

This invention relates to certain novel analogs of the naturally occurring prostaglandins. In particular, it relates to novel prostaglandin 5-indanyl esters and various novel intermediates useful in their preparation.

The prostaglandins are C-20 unsaturated fatty acids which exhibit diverse physiological effects. For instance, the prostaglandins of the E and A series are potent vasodilators (Bergstrom, et al., *Acta Physiol. Scand.* 64:332–339, 1965 and Bergstrom, et al., *Life Sci.* 6:449–455, 1967). This relaxant effect on small blood vessels probably accounts for the fall in systemic arterial blood pressure (vasodepression) observed on intravenous injection of $PGE_1$ and $PGA_1$ (Weeks and King, *Federation Proc.* 23:327; Bergstrom et al., 1965, op cit.; Carlson, et al., *Acta Med. Scand.* 183:423–430, 1968; and Carlson, et al., *Acta Physiol. Scand.* 75:161–169, 1969). Another well known physiological action for $PGE_1$ and $PGE_2$ is as a bronchodilator (Cuthbert, *Brit. Med. J.* 4:723–726, 1969).

Another important physiological role for the natural prostaglandins is in connection with the reproductive cycle. $PGE_2$ is known to possess the ability to induce labor (Karim, et al., *J. Obstet Gynaec. Brit. Cwlth.* 77:200–210, 1970), to induce therapeutic abortion (Bygdeman, et al., *Contraception*, 4, 293 (1971) and to be useful for control of fertility (Karim, *Contraception*, 3, 173 (1971). Patents have been obtained for several prostaglandins of the E and F series as inducers of labor in mammals (Belgian Pat. No. 754,158 and West German Pat. No. 2,034,641), and on $PGF_1$, $F_2$, and $F_3$ for control of the reproductive cycle (South African Pat. No. 69/6089).

Still other known physiological activities for $PGE_1$ are in the inhibition of gastric acid secretion (Shaw and Ramwell, In: *Worcester Symp. on Prostaglandins*, New York, Wiley, 1968, p. 55–64) and also of platelet aggregation (Emmons, et al., *Brit. Med. J.* 2:468–472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., *Acta. Physiol. Scand.*, 81, 396 (1971) and references cited therein).

It was, of course, considered desirable to create analogs of the prostaglandins which would have physiological activites equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (see *Lancet*, 536, 1971).

SUMMARY OF THE INVENTION

The novel compounds of this invention, the 5-indanyl esters of prostaglandins of the A-, E, or F-series, in which the 15β-hydrogen may be replaced by a 15β-lower alkyl group if desired, uniquely satisfy the above mentioned requirements. That is, they possess activity profiles comparable to the parent prostaglandins and they exhibit a longer duration of action than the parent prostaglandins.

The present invention comprises novel prostaglandins of the formulae:

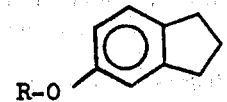

wherein R is

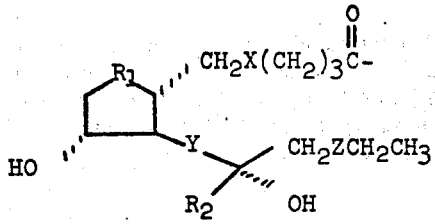

or

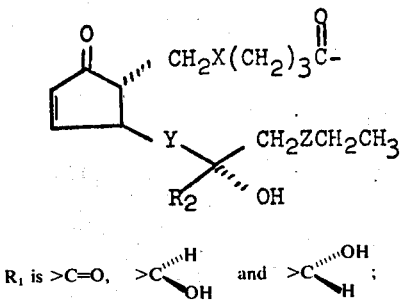

$R_1$ is $>C=O$, $>C\stackrel{H}{\underset{OH}{\diagdown}}$ and $>C\stackrel{OH}{\underset{H}{\diagdown}}$;

$R_2$ is hydrogen or $C_1$—$C_4$ lower alkyl;
X is $CH_2CH_2$ or cis $CH=CH$;
Y is $CH_2CH_2$ or trans $CH=CH$; and
Z is $CH_2CH_2$ or cis $CH=CH$, provided that when Z is cis $CH=CH$, X is cis $CH=CH$, and Y is Trans $CH=CH$;

and novel intermediates of the formula:

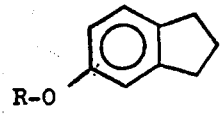

wherein R is:

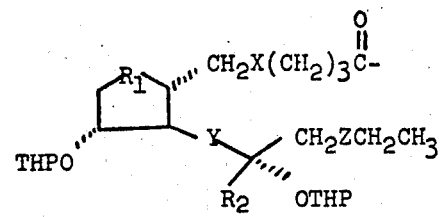

wherein all of the substituents are as defined above and THP is 2-tetrahydropyranyl.

Preferred are prostaglandins of the A, E, and F series of the above formulae and especially preferred are $PGE_2$ and $PGF_2$ α of the above formulae.

It will be understood that as herein used, the expression "prostaglandin of the 'zero' series," for example $PGE_0$, refers to prostaglandin in which the 5–6 and 13–14 double bonds have been saturated; i.e.: $PGE_0$ is 5–6, 13–14, tetrahydro $PGE_2$. In addition, the phrases "one series" or "two series" as herein employed refer to the degree of unsaturation in the side chains, e.g., $PGE_2$, $PGA_2$ and $PGF_2\alpha$, are prostaglandins of the two series whereas $PGE_1$, $PGF_1\alpha$ and $PGA_1$ are prostaglandins of the one series. As used herein and in the claims, the term prostaglandin is understood to embrace both epimers at $C_{15}$. Furthermore as herein employed the phrase lower "alkyl group" refers to alkyl groups containing from 1 to 4 carbon atoms.

It will be understood by those skilled in the art that in structures depicting hemiacetals, no sterochemistry is implied at the lactol carbon.

DETAILED DESCRIPTION OF THE INVENTION

For the first step in the preparation of the above named prostaglandin analogs, the appropriate known hemiacetal precursor (Corey, et al., *J. Am. Chem. Soc.*, 92, 397 (1970) is caused to react with (4-carbohydroxy-n-butyl)triphenylphosphoniumbromide, in a molar ratio of from about 1:2 to 1:5. The reaction will preferably be carried out at temperatures of about 25°–65° C. in an inert solvent such as dimethylsulfoxide and in an inert atmosphere, for a period of up to about 4 hours or until the reaction is essentially complete.

The 11,15Bis-THP-esters thus produced in the first step, as described above, are then caused to react with 5-indanol in the presence of a suitable dehydrating agent such as dicyclohexylcarbodiimide, in at least an equi-molar ratio for a period of up to about 24 hours. The reaction is preferably carried out at ambient temperature and the crude, oily product may be purified by column chromatography. These novel compounds may be converted by published procedures (Corey, et al., *J. Am. Chem. Soc.*, 93, 1490 (1971) to the 5-indanyl esters of any of the prostaglandins listed above. These procedures are further described in detail in the appended examples and the steps entailed are summarized in the flow sheet below. Flow sheet A outlines the preparation of the 5-indanyl ester of $PGF_2\alpha$, $PGF_2\beta$, $PGE_2$, $PGA_2$, $PGF_1\alpha$, $PGF_1\beta$, $PGE_1$, $PGA_1$, 13,14-dihydro $PGF_1\alpha$, 13,14-dihydro $PGF_1\beta$, 13,14-dihydro $PGE_1$ and 13,14-dihydro $PGA_1$. Flow sheet B outlines the preparation of the 5-indanyl ester of 13,14-dihydro $PGF_2\alpha$, 13,14-dihydro $PGF_2\beta$, 13,14-dihydro $PGE_2$, and 13,14-dihydro $PGA_2$.

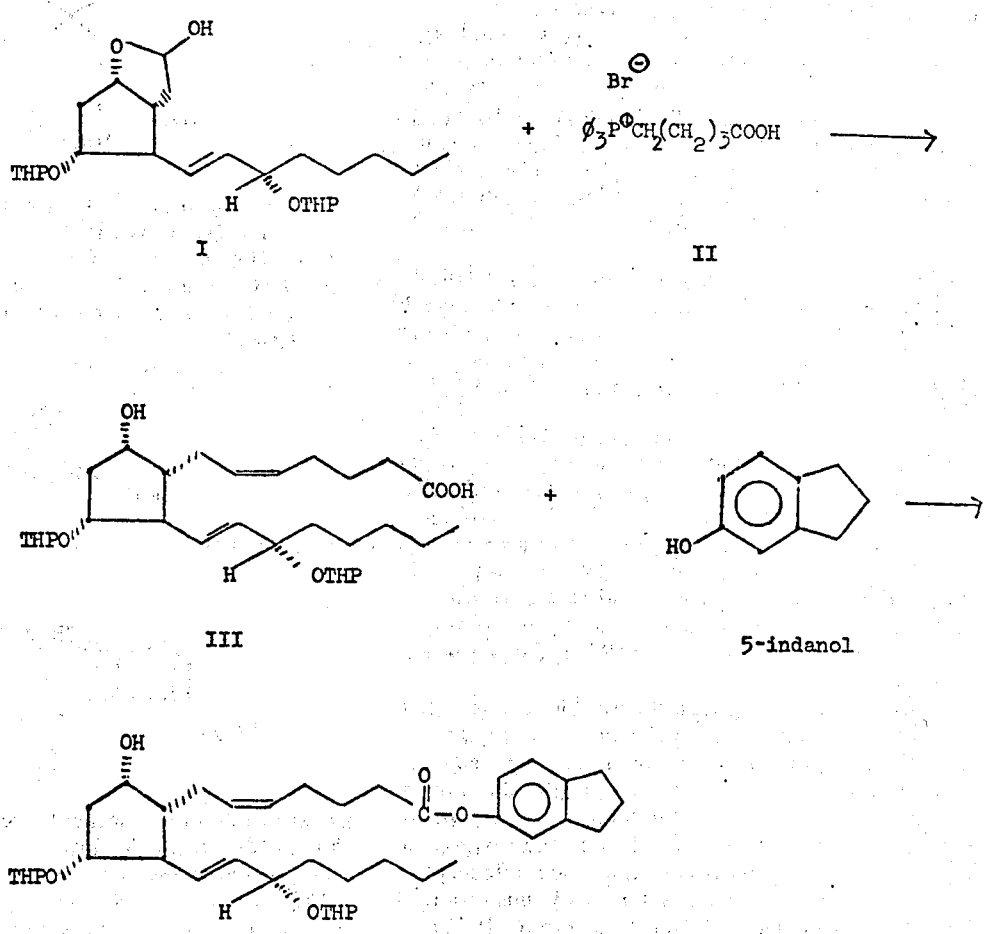

REACTION SCHEME A

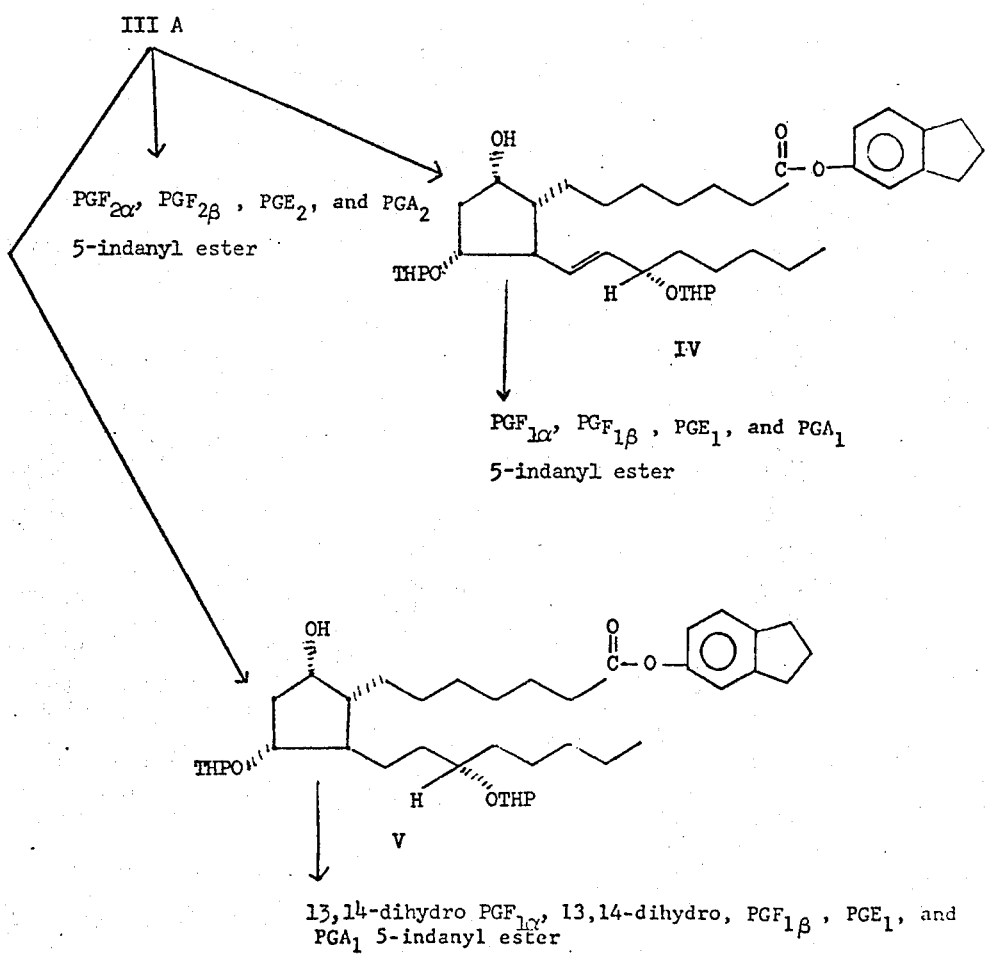
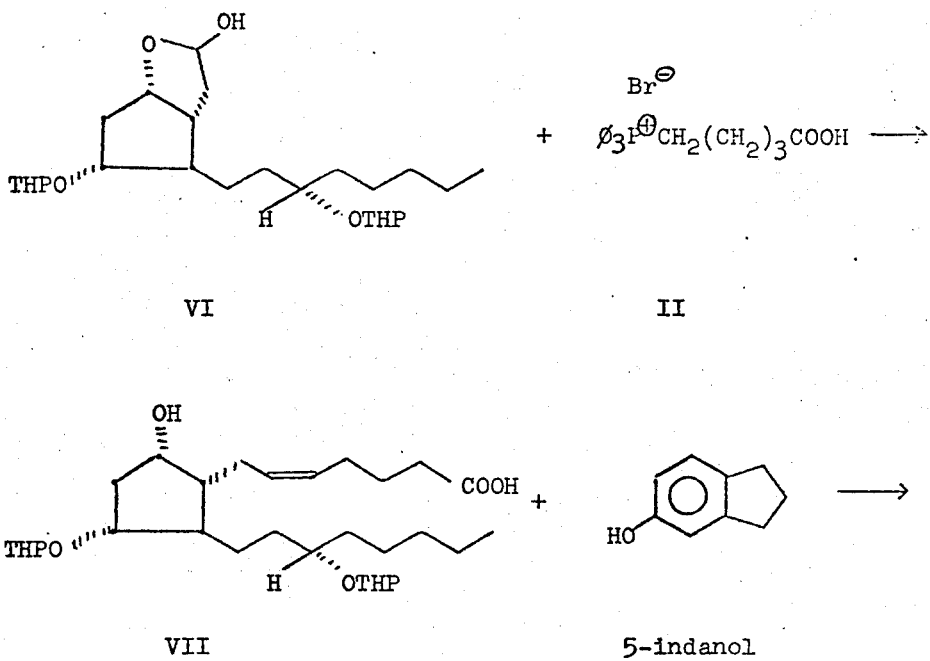
REACTION SCHEME B

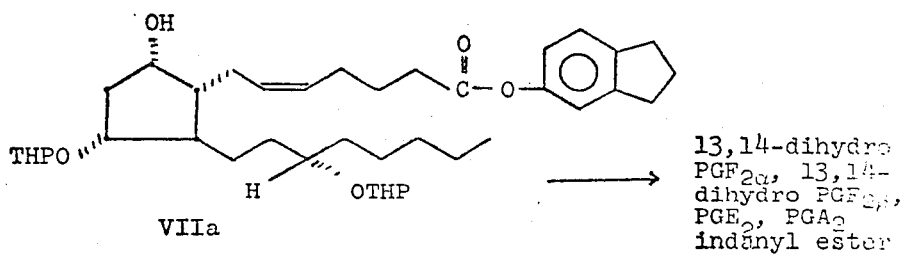

VIIa → 13,14-dihydro PGF$_{2\alpha}$, 13,14-dihydro PGF$_{2\beta}$, PGE$_2$, PGA$_2$ indanyl ester As shown in Reaction Scheme A, Hemiacetal I is caused to react with reagent II to produce III, the bis-THP ether of PGF$_2$ $_\alpha$.

III → IIIa involves reaction with 5-indanol in the presence of dicyclohexylcarbodiimide, concentration, and column chromatography.

IIIa → 5-indanyl-PGF$_2$ $_\alpha$ involves hydrolysis with aqueous acetic acid, concentration, and purification by column chromatography.

IIIa → 5-indanyl-PGE$_2$ requires treatment with Jones' reagent to form a second intermediate before the acid treatment and purification as above.

IIIa → 5-indanyl PGF$_1$ $_\beta$ follows exactly the same method as outlined for the PGF$_2$$_\beta$ series.

5-Indanyl-PGA$_2$ is obtained by treating 5-indanyl PGE$_2$ with formic acid, concentration, and purification by column chromatography.

IIIa → 5-indanyl-PGF$_1$ $_\alpha$ requires a selective reduction with palladium on carbon and methanol to produce IV which may then be hydrolyzed with aqueous acetic acid, and purified as above.

IIIa → 5-indanyl PGF$_2$ $_\beta$ requires treatment with Jones' reagent to form a second intermediate and reduction of this intermediate with sodium borohydride before the acid treatment and purification as above.

IIIa → 5-indanyl-PGE$_1$ → 5-indanyl-PGA$_1$ follows exactly the same method as outlined for the PGE$_2$-PGA$_2$ series above.

IIIa → 5-indanyl-13,14-dihydro PGF$_1$ $_\alpha$ requires a reduction with palladium on carbon and methanol to produce V which is then hydrolyzed with aqueous acetic acid, and purified as above.

To produce the other 13,14-dihydro derivatives, one follows the procedures outlined above.

Referring now to Reaction Scheme B, Hemiacetal VI is caused to react with reagent II to produce VII, the bis-THP ether of 13,14-dihydro PGF$_2$ $_\alpha$. VII is reacted with 5-indanol, as above, to produce VIIa.

VIIa → 5-indanyl-13,14-dihydro PGF$_2$ $_\alpha$ involves hydrolysis with aqueous acetic acid, concentration, and purification by column chromatography.

VIIa → 5-indanyl-13,14-dihydro PGE$_2$ requires treatment with Jones' reagent to form a second intermediate before acid treatment and purification as above.

VIIa → 5-indanyl-13,14-dihydro PGF$_2$ $_\beta$ requires treatment with Jones' reagent to form a second intermediate and reduction of this intermediate with sodium borohydride before its acid treatment and purification as above.

5-Indanyl-13,14-dihydro PGA$_2$ is obtained by treating 5-indanyl-13,14-dihydro PGE$_2$ with formic acid, concentrating, and purifying by column chromatography.

To produce the 15-lower alkyl derivatives of all of the above mentioned prostaglandin indanyl esters, one merely employs hemiacetal I or the hemiacetal VI with a lower alkyl moiety substituted for the hydrogen in the 15-position and proceeds as above to produce the desired compound.

The C$_{15}$ epimers of hemiacetal I or hemiacetal VI can be employed as precursors to produce the C$_{15}$ epimers of all of the prostaglandin esters described above by the same methods as are shown above.

To produce PGF$_3$ $_\alpha$ and PGE$_3$ indanyl esters, the known hemiacetal VIII (E. J. Corey, et al., *J. Amer. Chem. Soc.*, 93, p. 1490, 1971) is employed as the starting material and all of the other reaction steps are identical to those given above.

TABLE I

| Compound Used | Approx. Threshold doses for spasmogenic effect on isolated smooth muscle ng/ml. | | Conc. for 50% Inhibition of NE[1] induced lipolysis in isolated rat fat cells (NE 2.5×10$^{-7}$M) | Histamine Induced Bronchospasm in guinea pig Approx. % protection by 100 g/ml. aerosol dose | Approx. Threshold dose for Effect on Anesthesized Dog Blood Pressure g/kg iv. (−) - depressor (+) - pressor | Estimated Relative Potency (to PGE$_1$) for 50% Inhibition of ADP-induced Aggregation of Rabbit Platelets in vitro |
|---|---|---|---|---|---|---|
| | Guinea Pig Ileum | Rat Uterus | | | | |
| PGE$_2$ | 10–30 | 10–30 | 4×10$^{-7}$ | 75–85 | 0.16 (−) | 0.007 |
| PGE$_2$ Methyl Ester | 50–100 | | 1.4×10$^{-6}$ | | 0.4 (−) same duration of action as for PGE$_2$ | 0.007 |
| PGE$_2$ Indanyl Ester | 10–50 | 30–50 | 2×10$^{-7}$ | 75–85 | 0.16 (−) Effect 5–10 times longer duration than for PGE$_2$ | 0.02 |

[1]Norepinephrine

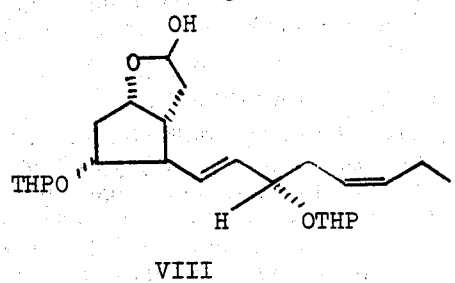

VIII

As the literature cited under "Background of the Invention" establishes, the natural prostaglandins are known to exhibit a spectrum of physiological activities. In numerous in vivo and in vitro tests we have demonstrated that the prostaglandin 5-indanyl esters have the same physiological activities as exhibited by the natural prostaglandins but are more selective, orally efficacious, and longer acting. These tests include, among others, a test for effect on isolated smooth muscle from guinea pig ileum, and rat uterus, a test for inhibition of norepinephrine induced lipolysis in isolated rat fat cells, a test for effect on histamine induced bronchospasm in guinea pig, a test for effects on dog blood pressure, a test for relative potency for 50% inhibition of ADP-induced aggregation of rabbit platelets, in vitro, a test for in vivo diarrhea effects in mice, and a test for oral antiulcer activity in stressed rats. Results of these tests are presented in Table I, below. The prolonged hypotensive effect, relative to $PGE_2$, exhibited by the $PGE_2$ 5-indanyl ester demonstrates particular utility for the E series of indanyl esters as antihypertensive agents. In addition, the methyl ester of $PGE_2$ has been prepared and tested, and the compounds of this invention are much superior to this simple ester in the various tests employed, particularly in regard to its blood pressure effects.

The $PGE_2$ 5-indanyl ester, unlike $PGE_2$, exhibits potent, oral antiulcer activity in stressed rats which demonstrates a unique utility for the E series of indanyl esters as antiulcer agents. In addition, the $PGE_2$ 5-indanyl ester displayed only 1/10 the diarrheal activity of $PGE_2$ in mice indicating that the $PGE_2$ 5-indanyl ester should display fewer gastrointestinal side-effects than $PGE_2$.

The $PGF_{2\alpha}$ 5-indanyl ester and $PGF_{2\alpha}$ exhibit comparable in vitro guinea pig uterine spasmogenic activity while the $PGF_{2\alpha}$ 5-indanyl ester exhibits less diarrheal activity in mice than $PGF_{2\alpha}$. These data demonstrate particular utility for the F series of indanyl esters as antifertility agents, abortificients, and inducers of labor.

The new compounds of this invention can be used in a variety of pharmaceutical preparations and they may be administered by a variety of routes, such as intravenous, oral and topical including aerosol, intravaginal, and intranasal among others.

The natural prostaglandins of the E and F series are well known agents for the induction of abortion, and the corresponding prostaglandin 5-indanyl esters share this utility. For such treatment an aqueous suspension of $PGE_2$ or $PGF_{2\alpha}$ 5-indanyl ester is appropriately administered at a level of from about 0.1–5.0 mg/dose for $PGE_2$ 5-indanyl ester or 5.0–50 mg/dose for $PGF_{2\alpha}$ 5-indanyl ester with from 1 to 7 oral doses per day being employed in either case.

If an intravaginal treatment for abortion induction is desired, a suitable agent is a sterile ethanolic solution of either of these two prostaglandin 5-indanyl esters or lactose tablets of the same two agents. In such treatments suitable doses are from 15–200 mg/dose for $PGE_2$ 5-indanyl ester or from 35–500 mg/dose for $PGF_{2\alpha}$ 5-indanyl ester with 1 or 2 doses being employed.

In cases where a midterm abortion is necessary, an effective agent is an ethanol-dextrose solution of $PGE_2$ 5-indanyl ester administered as an intravenous infusion. A suitable dosage is from about 5–500 µg/min administered for a period of from 1–24 hours.

If an intra-amniotic treatment for midterm abortion is necessary, an effective agent is a sterile ethanolic solution of either $PGE_2$ or $PGF_{2\alpha}$ 5-indanyl ester administered directly into the amniotic sac by means of a polyethylene catheter. A suitable dose is from 0.5–5.0 mg/dose for $PGE_2$ 5-indanyl ester or 5–50 mg/dose for $PGF_{2\alpha}$ 5-indanyl ester with from 1 to 5 doses administered.

Another use for the prostaglandin 5-indanyl esters is as an inducer of labor. For this purpose an ethanol-saline solution of $PGE_2$ 5-indanyl ester is employed as an intravenous infusion in the amount of from about 3–100 µg/kg/min for from 5–24 hours.

Still other applications for the E-series prostaglandin 5-indanyl esters are to produce bronchodilation or to increase nasal patency. An appropriate dosage form for this use is an aqueous ethanolic solution of $PGE_2$ or $PGE_1$ 5-indanyl ester employed as an aerosol using fluorinated hydrocarbons as propellant in the amount of from about 3–500 µg/dose.

A use for A-series 5-indanyl esters is as antihypertensive agents. For such a treatment an ethanol solution of $PGA_1$ or $PGA_2$ 5-indanyl ester is appropriately administered as an intravenous infusion at about 1–30 µg/kg/min.

An application for the E-series prostaglandin 5-indanyl esters are as antiulcer agents. An appropriate dosage form for this use is a solid formulation of $PGE_2$, $PGE_1$ or $PGE_0$ 5-indanyl ester administered orally in the amount of from 0.1–10 mg/dose with from 1 to 4 doses administered daily.

The utility of the 15-lower alkyl substituted prostaglandin indanyl esters generally parallels that of the 15-desalkyl derivatives.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired, these pharmaceutical compositions may contain auxiliary subtances such as preserving agents, wetting agents, stabilizing agents, or other therapeutic agents such as antibiotics.

It will be seen that the formulae appearing in the foregoing depict optically active compounds. It will be clear, however, that the corresponding racemates will exhibit valuable biological activity by virtue of their content of the above-mentioned biologically active optical isomer, and it is intended that such racemates also be embraced by the foregoing formulae herein and in the appended claims. The racemic mixtures are readily prepared by the same methods employed herein to synthesize the optically active species, by mere substitution of corresponding racemic precursors in place of optically active starting materials.

The following examples are merely illustrative, and in no way limit the scope of the appended claims. All

EXAMPLE I

To a solution of 12.0 g (27.0 mmoles) of 5-triphenylphosphoniopentanoic acid in 24 ml. of dimethyl sulfoxide was added dropwise 25.6 ml (51.2 mmoles) of a 2.0 M solution of sodium methylsulfinylmethide in dimethyl sulfoxide. To the resultant red ylide solution was added over the course of 1.0 hour a solution of 4.75 g (10.8 mmoles) of the known 2-[5α-hydroxy-3α-(tetrahydropyran-2-yloxy)-2β-(3α-tetrahydropyran-2-yloxy)-trans-1-octen-1-yl)cyclopent-1α-yl]acetaldehyde, γ-hemiacetal in 33 ml. of dimethyl sulfoxide. After being stirred for an additional 1.0 hour the reaction was poured onto 300 ml. of ice-water. The basic aqueous solution was extracted with a 2:1 mixture of ethyl acetate:ether (2 × 150 ml.). The cold aqueous layer was then covered with ethyl acetate and was acidified to pH ~ 3 with 10% aqueous hydrochloric acid. The acidified aqueous layer was further extracted with ethyl acetate (2 × 100 ml). The combined organic extracts were washed with water (1x), were dried (anhydrous magnesium sulfate), and were concentrated to afford a crude residue. Purification of this crude residue by silica gel chromatography using ethyl acetate as eluent afforded 4.24 g (75.5% yield) of the known 9α-hydroxy-11α,15α-bis-(tetrahydropyran-2-yloxy)-cis-5-trans-13-prostadienoic acid as a colorless oil.

In a similar manner 2-[5α-hydroxy-3α-(tetrahydropyran-2-yloxy)-2β-(3α-(tetrahydropyran-2-yloxy)-3β-lower alkyl-trans-1-octen-1-yl)cyclopent-1α-yl]acetaldehyde, γ-hemiacetal may be employed in the above reaction to provide 9α-hydroxy-11α,15α-bis-(tetrahydropyran-2-yloxy)-15β-lower alkyl-cis-5-trans-13-prostadienoic acid which is a suitable starting material for the synthesis of the 5-indanyl esters of the 15-lower alkyl $PGF_{1\alpha}$, $PGF_{1\beta}$, $PGE_1$, $PGA_1$, $PGF_{2\alpha}$, $PGE_2$, $PGF_{2\beta}$, $PGA_2$, 13,14-dihydro $PGF_{1\alpha}$, 13,14-dihydro $PGE_1$, 13,14-dihydro $PGF_{1\beta}$, and 13,14-dihydro $PGA_1$ by the procedures of Examples II–VII.

In a similar manner 2-[5α-hydroxy-3α-(tetrahydropyran-2-yloxy)-2β-(3α-(tetrahydropyran-2-yloxy)oct-1-yl)cyclopent-1α-yl]acetaldehyde, γ-hemiacetal may be employed in the above reaction to provide 9α-hydroxy-11α,15α-bis-(tetrahydropyran-2-yloxy)-cis-5-prostenoic acid which is suitable starting material for the synthesis of the 5-indanyl esters of the 13,14-dihydro $PGF_{2\alpha}$, 13,14-dihydro $PGF_{2\beta}$, 13,14-dihydro $PGE_2$ and 13;14-dihydro $PGA_2$ by the procedures of Examples II–V.

In a similar manner 2-[5α-hydroxy-3α-(tetrahydropyran-2-yloxy)-2β-(3β-lower alkyl-3α-(tetrahydropyran-2-yloxy)oct-1-yl)cyclopent-1α-yl]acetaldehyde, γ-hemiacetal may be employed in the above reaction to provide 9α-hydroxy-11α,15α-bis-(tetrahydropyran-2-yloxy)-15β-lower alkyl-cis-5-prostenoic acid which is a suitable starting material for the synthesis of the 5-indanyl esters of the 13,14-dihydro-15-lower alkyl $PGF_{2\alpha}$, 13,14-dihydro-15-lower alkyl $PGF_{2\beta}$, and 13,14-dihydro-15-lower alkyl $PGE_2$, and 13,14-dihydro-15-lower alkyl $PGA_2$ by the procedures of Examples II–V.

In a similar manner 2-[5α-hydroxy-3α-(tetrahydropyran-2-yloxy)-2β-(3α-(tetrahydropyran-2-yloxy)-cis-5-trans-1-octadien-1-yl)cyclopent-1α-yl]acetaldehyde, γ-hemiacetal may be employed in the above reaction to provide 9α-hydroxy-11α,15α-bis-(tetrahydropyran-2-yloxy)-cis-5-trans-13-cis-17-prostatrienoic acid which is a suitable starting material for the synthesis of the 5-indanyl esters of $PGF_{3\alpha}$ and $PGE_3$ by the procedures II–IV.

EXAMPLE II

A mixture of 390 mg. (0.746 mmole) of the known 9α-hydroxy-11α,15α-bis-(tetrahydropyran-2-yloxy)-cis-5-trans-13-prostadienoic acid, 308 mg. (1.49 mmole) of dicyclohexylcarbodiimide, and 200 mg. (1.49 mmole) of 5-indanol (m.p. 53°–55°) in 7.5 ml. of methylene chloride was stirred at ambient temperature for 18 hours and then was concentrated by rotary evaportion. The resultant semi-solid was triturated with hexane and the hexane triturate was concentrated to afford a colorless oil. The crude oily product was purified by column chromatography on silica gel (Baker 'Analyzed' Reagent) using first benzene then a 4:1 mixture of benzene:ethyl acetate as eluents. After removal of higher $R_f$ impurities the product, 5-Indanyl 9α-hydroxy-11α,15α-bis-(tetrahydropyran-2-yloxy)-cis-5-trans-13-prostadienoate was collected weighing 213 mg. (44.8% yield).

The ir spectrum (CHCl$_3$) exhibited a strong absorption at 5.74 μ (ester carbonyl). The nmr spectrum (CDCl$_3$) exhibited a multiplet at 7.30–6.65 δ for the aromatic protons, a multiplet at 5.68–5.32 δ for the olefinic protons, a broad singlet at 4.70 δ for the OH, multiplets at 4.36–3.27 δ for the OCH, a multiplet at 3.12–2.72 δ for the benzylic protons, and multiplets at 2.72–0.67 δ for the remaining protons.

EXAMPLE III

To a solution, cooled to −20°, of 213 mg. (0.335 mmole) of the chromatographed, oily hydroxyester prepared above in Example I in 3.0 ml. of acetone was added dropwise 0.112 ml. (0.300 mmole) of Jones' reagent. The mixture was stirred at −15° to −20° under nitrogen for 20 minutes then was quenched by the addition of 0.112 ml. of 2-propanol. The mixture was stirred in the cold for 5 minutes then was diluted with ethyl acetate. The organic solution was washed with water (3x), was dried (anhydrous magnesium sulfate), and was concentrated to afford the colorless, oily 5-Indanyl 9-oxo-11α,15α-bis-(tetrahydropyran-2-yloxy)-cis-5-trans-13-prostadienoate weighing 186 mg. (87.3% yield).

The ir spectrum (CHCl$_3$) exhibited a strong absorption at 5.74 μ (ester and ketone carbonyls).

EXAMPLE IV

A solution of 186 mg. (0.293 mmole) of the crude keto ester prepared above in Example II in 3.0 ml. of a 65:35 mixture of acetic acid:water was stirred at 40° ± 2° under nitrogen for 6.0 hours then was concentrated by rotary evaporation. The crude oily product was purified by column chromatography on silica gel (Baker 'Analyzed' Reagent) using increasing amounts of ethyl acetate in methylene chloride. After elution of high $R_f$ impurities the semi-solid product, 5-indanyl 9-oxo-11α,15α-dihydroxy-cis-5-trans-13-prostadienoate was collected weighing 62 mg. (45.2% yield). Crystallization from hexane-ether afforded white needles melting at 45.5°–48.0°. This product is the 5-indanyl ester of prostaglandin E$_2$.

The ir spectrum (CHCl$_3$) exhibited a strong absorption at 5.74 μ (ester and ketone carbonyls) and a weak absorption at 10.3 μ (trans double bond). The nmr spectrum (CDCl$_3$) exhibited a multiplet at 7.29–6.66 δ for the aromatic protons, a multiplet at 5.67–5.22 δ for the olefinic protons, a multiplet at 4.32–3.63 δ for the OCH and OH, a triplet at 2.90 δ (J = 6 cps) for the benzylic protons, and multiplets at 2.72–0.67 δ for the remaining protons.

EXAMPLE IVA

To a solution under nitrogen of 640 mg (1.0 mmole) of the 5-indanyl 9-oxo-11α,15α-bis-(tetrahydropyran-2-yloxy)-cis-5-trans-13-prostadienoate in 10 ml. of dry dimethoxyethane is added dropwise 1.0 ml of a 0.5 M solution of zinc borohydride in dimethoxyethane. The solution is stirred at room temperature for 1.0 hour then is quenched by the dropwise addition of a saturated sodium bitartrate solution until gas evolution ceases. The quenched solution is diluted with methylene chloride, is dried (anhydrous magnesium sulfate), and is concentrated to afford a mixture of 5-indanyl 9α- and 9β-hydroxy-11α,15α-bis-(tetrahydropyran-2-yloxy)-cis-5-trans-13-prostadienoate.

EXAMPLE IVB

A solution of 570 mg of the 5-indanyl 9α- and 9β-hydroxy-11α,15α-bis-(tetrahydropyran-2-yloxy)-cis-5-trans-13-prostadienoate mixture prepared above in 10 ml of a 65:35 mixture of acetic acid:water is stirred under nitrogen at room temperature overnight. Concentration of the reaction mixture, followed by chromatographic purification of the crude residue provides the 5-indanyl ester of prostaglandin $F_{2\alpha}$ and the 5-indanyl ester of prostaglandin $F_{2\beta}$.

EXAMPLE V

A solution of 20 mg of the product of Example IV in 2 ml of a 1:1 mixture of 97% formic acid:methylene chloride is stirred at room temperature under nitrogen for 2.0 hours then is diluted with toluene (10 ml) and is concentrated by rotary-evaporation. Purification of the residue by silica gel chromatography provides the 5-indanyl 9-oxo-15α-hydroxy-$\Delta^{10,11}$-cis-5-trans-13-prostatrienoate, the 5-indanyl ester of $PGA_2$.

EXAMPLE VI

A heterogeneous mixture of 0.196 g of 9α-hydroxy-11α,15α-bis-(tetrahydropyran-2-yloxy)-cis-5-trans-13-prostadienoic acid, the product from Example I and 50 mg of 5% palladium on carbon in 10 ml of absolute methanol cooled to −20° was stirred 1 atmosphere of hydrogen for 5.5 hours. The reaction was then filtered (Celite) and concentrated to afford the 9α-hydroxy-11α,15α-bis-(tetrahydropyran-2-yloxy)-trans-13-prostenoic acid. This product is suitable for the preparation of the 5-indanyl esters of $PGF_{1\alpha}$, $PGF_{1\beta}$, $PGE_1$ and $PGA_1$ by the procedures of Examples II–V.

In a similar manner 9α-hydroxy-11α,15α-bis-(tetrahydropyran-2-yloxy)-15β-lower alkyl-cis-5-trans-13-prostadienoic acid, prepared as described in Example I, may be employed in the above reaction to provide 9α-hydroxy-11α,15α-bis-(tetrahydropyran-2-yloxy)-trans-13-prostenoic acid which is a suitable starting material for the synthesis of the 5-indanyl esters of the 15-lower alkyl $PGF_{1\alpha}$, $PGF_{1\beta}$, $PGE_1$, and $PGA_1$ by the procedures of Examples II–V.

EXAMPLE VII

A heterogeneous mixture of 200 mg of 9α-hydroxy-11α,15α-bis-(tetrahydropyran-2-yloxy)-cis-5-trans-13-prostadienoic acid, from Example I and 50 mg of 5% palladium on carbon in 10 ml of absolute methanol is stirred at room temperature under 1 atmosphere of hydrogen for 2.5 hours. The reaction mixture is then filtered (Celite) and is concentrated to provide 9α-hydroxy-11α,15α-bis-(tetrahydropyran-2-yloxy)-prostanoic acid. This product is suitable for the preparation of the 5-indanyl esters of 13,14-dihydro $PGF_{1\alpha}$, $PGF_{1\beta}$, $PGE_1$ and $PGA_1$ by the procedures of Examples II–V.

In a similar manner 9α-hydroxy-11α,15α-bis-(tetrahydropyran-2-yloxy)-15β-lower alkyl-cis-5-trans-13-prostadienoic acid, prepared in Example I, may be employed in the above reaction to provide 9α-hydroxy-11α,15α-bis-(tetrahydropyran-2-yloxy)prostanoic acid which is a suitable starting material for the synthesis of the 5-indanyl esters of the 15-lower alkyl-13,14-dihydro $PGF_{1\alpha}$, $PGF_{1\beta}$, $PGE_1$ and $PGA_1$ by the procedures of Examples II–V.

EXAMPLE VIII

A heterogeneous mixture of 2.24 g (5.0 mmoles) of the known 2-[5α-hydroxy-3α-p-phenylbenzoyloxy-2β-(3β-hydroxy-trans-1-octen-1-yl)cyclopent-1α-yl]acetic acid, γ-lactone and 0.680 g (5.0 mmoles of anhydrous potassium carbonate in 22 ml of absolute methanol was stirred at room temperature under nitrogen for 2.0 hours. The reaction mixture was then cooled in ice and was quenched by the addition of 10 ml of 1.0 N aqueous hydrochloric acid. The quenched mixture was diluted with water (22 ml.) and filtered to remove the precipitated methyl p-phenylbentoate. The filtrate was extracted with ethyl acetate (3 × 50 ml); the combined organic extracts were washed with saturated sodium bicarbonate and saturate brine, were dried (anhydrous magnesium sulfate), and were concentrated to afford the desired 2-[3α,5α-dihydroxy-2β-(3β-hydroxy-trans-1-octen-1-yl)cyclopent-1α-yl]acetic acid, γ-lactone as a viscous oil weighing 1.17 g (87.4% yield). The ir and nmr spectra of the product were superimposable on those of the known 15α-epimer.

EXAMPLE IX

To a solution of 1.17 g. (4.37 mmoles) of the 2-[3α,5α-dihydroxy-2β-(3β-hydroxy-trans-1-octen-1-yl)cyclopent-1α-yl]acetic acid, γ-lactone prepared above and 1.17 ml of 2,3-dihydropyran in 12 ml of methylene chloride was added 12 mg of p-toluenesulfonic acid monohydrate. The reaction was stirred under nitrogen at room temperature for 15 minutes then was diluted with ether (100 ml). The diluted solution was washed with saturated sodium bicarbonate and saturated brine, was dried (anhydrous magnesium sulfate), and was concentrated to afford the desired 2-[5α-hydroxy-3α-(tetrahydropyran-2-yloxy)-2β-(3β-(tetrahydropyran-2-yloxy)-trans-1-octen-1-yl)cyclopent-1α-yl]acetic acid, γ-lactone as a viscous oil weighing 2.10 g (>100% yield). The ir and nmr spectra were superimposable on those of the known 15α-epimer.

EXAMPLE X

To a solution, cooled to −78° under nitrogen, of 1.90 g (4.37 mmoles) the 2-[5α-hydroxy-3α-(tetrahydropyran-2-yloxy)-2β-(3β-(tetrahydropyran-2-yloxy)-trans-1-octen-1-yl)cyclopent-1α-yl]-acetic acid, γ-lactone prepared above in 25 ml of dry toluene was added dropwise 5.92 ml of a 20% solution of diisobutylaluminum hydride in hexane (Alfa Inorganics). The reaction was stirred for 45 minutes at −78° then was quenched by the dropwise addition of methanol until gas evolution ceased. The quenched reaction was let warm to room temperature, was diluted with ether, was washed with a 50% sodium potassium tartrate solution and with saturated brine, was dried (anhydrous magnesium sulfate), and was concentrated to provide a viscous, yellow oil which was purified by column chromatography (Baker Silica Gel 60–200 mesh) using mixture of benzene:ethyl acetate as eluents. After removal of less polar impurities the desired 2-[5α-hydroxy-3α-(tetrahydropyran-2-yloxy)-2β-(3β-(tetrahydropyran-2-yloxy)-trans-1-octen-1-yl)cyclopent-1α-yl]acetaldehyde, γ-hemiacetal was collected as a colorless oil weighing 1.59 g (83.5% yield). The ir and nmr spectra were superimposable on those of the known 15α-epimer.

EXAMPLE XI

To a solution of 4.83 g (10.9 mmoles) of 5-triphenylphosphoniopentanoic acid in 8 ml of dimethyl sulfoxide was added dropwise 15.1 ml (20.8 mmoles) of a 1.38 M solution of sodium methylsulfinylmethide in dimethyl sulfoxide. To the resultant ylide solution was added over the course of 20 minutes a solution of 1.59 g (3.63 mmoles) of the 2-[5α-hydroxy-3α-(tetrahydropyran-2-yloxy)-2β-(3β-(tetrahydropyran-2-yloxy)-trans-1-octen-1-yl)cyclopent-1α-yl]acetaldehyde, γ-hemiacetal in 6 ml of dimethyl sulfoxide. After being stirred overnight, the reaction was poured onto ice-water. The aqueous solution was overlaid with ethyl acetate and was acidified (pH ~ 3) with 10% hydrochloric acid. The acidified aqueous layer was further extracted with ethyl acetate (3x). The combined organic extracts were washed with water (1x) and saturated brine (1x), were dried (anhydrous magnesium sulfate), and were concentrated to afford a crude residue which was purified by silica gel chromatography using chloroform as eluent. After removal of less polar impurities the desired 9α-hydroxy-11α,15β-bis-(tetrahydropyran-2-yloxy)-cis-5-trans-13-prostadienoic acid was collected as a colorless oil weighing 1.99 g. (>100% yield). The ir and nmr spectra of the product were superimposable on those of the known 15α-epimer.

The above starting material may be converted into 15-epi PGF$_{2\alpha}$, PGF$_{2\beta}$, PGE$_2$, PGA$_2$, PGF$_{1\alpha}$, PGF$_{1\beta}$, PGE$_1$, PGA$_1$, 13,14-dihydro PGF$_{1\alpha}$, PGF$_{1\beta}$, PGE$_1$, and PGA$_1$.

EXAMPLE XII

A heterogeneous mixture of 1.72 g of the 2-[5α-hydroxy-3α-(tetrahydropyran-2-yloxy)-2β-(3β-(tetrahydropyran-2-yloxy)-trans-1-octen-1-yl)cyclopent-1α-yl]acetic acid, γ-lactone prepared above and 172 mg of 5% palladium on carbon in 170 ml of absolute methanol is stirred under 1 atmosphere of hydrogen for 4 hours. The reaction is then filtered (Celite) and concentrated to afford the desired 2-[5α-hydroxy-3α-(tetrahydropyran-2-yloxy)-2β-(3β-(tetrahydropyran-2-yloxy)-oct-1-yl)cyclopent-1α-yl]acetic acid, γ-lactone.

The material may be converted into the 15-epi-13,14-dihydro PGF$_{2\alpha}$, PGF$_{2\beta}$, PGE$_2$ and PGA$_2$.

What is claimed is:

1. A compound of the formula:

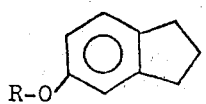

wherein R is

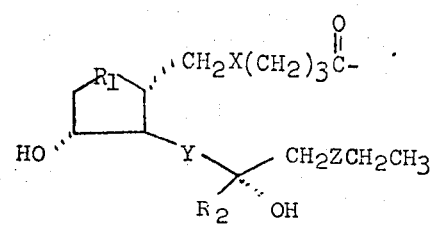

or

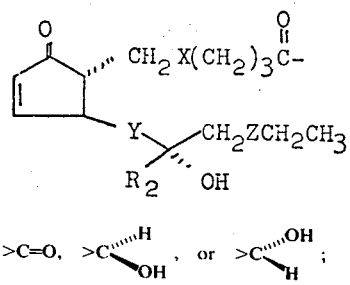

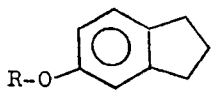

R$_2$ is hydrogen or C$_1$–C$_4$ lower alkyl;
X is CH$_2$CH$_2$ or cis CH=CH;
Y is CH$_2$CH$_2$ or trans CH=CH; and
Z is CH$_2$CH$_2$ or cis CH=CH, provided that when Z is cis CH=CH, X is cis CH=CH, and Y is trans CH=CH.

2. A compound according to claim 1 of the formula:

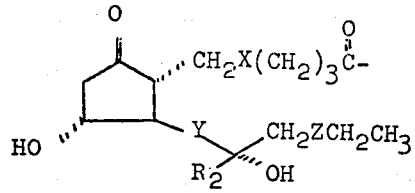

wherein R is:

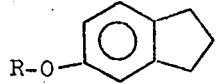

R$_2$ is hydrogen or C$_1$–C$_4$ lower alkyl;
X is CH$_2$CH$_2$ or cis CH=CH;
Y is CH$_2$CH$_2$ or trans CH=CH; and
Z is CH$_2$CH$_2$ or cis CH=CH, provided that when Z is cis CH=CH, X is cis CH=CH, and Y is trans CH=CH.

3. A compound according to claim 1 of the formula:

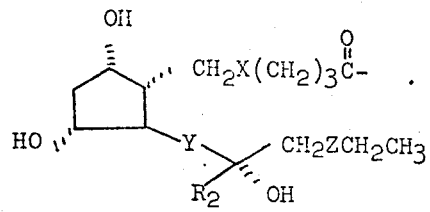

wherein R is

R$_2$ is hydrogen or C$_1$–C$_4$ lower alkyl;
X is CH$_2$CH$_2$ or cis CH=CH;
Y is CH$_2$CH$_2$ or trans CH=CH; and
Z is CH$_2$CH$_2$ or cis CH=CH, provided that when Z is cis CH=CH, X is cis CH=CH, and Y is trans CH=CH.

4. A compound according to claim 1 of the formula:

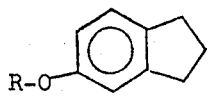

wherein R is

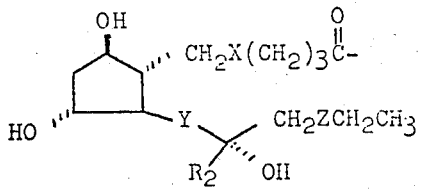

$R_2$ is hydrogen or $C_1$–$C_4$ lower alkyl;
X is $CH_2CH_2$ or cis CH=CH;
Y is $CH_2CH_2$ or trans CH=CH; and
Z is $CH_2CH_2$ or cis CH=CH, provided that when Z is cis CH=CH, X is cis CH=CH, and Y is trans CH=CH.

5. A compound according to claim 1 of the formula:

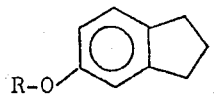

wherein R is

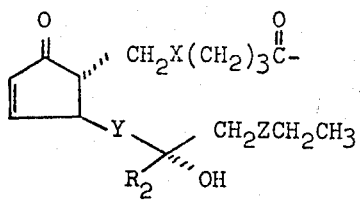

$R_2$ is hydrogen or $C_1$–$C_4$ lower alkyl;
X is $CH_2CH_2$ or cis CH=CH;
Y is $CH_2CH_2$ or trans CH=CH; and
Z is $CH_2CH_2$ or cis CH=CH, provided that when Z is cis CH=CH, X is cis CH=CH, and Y is CH=CH.

6. A compound according to claim 2 of the formula:

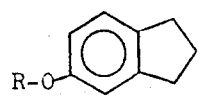

wherein R is

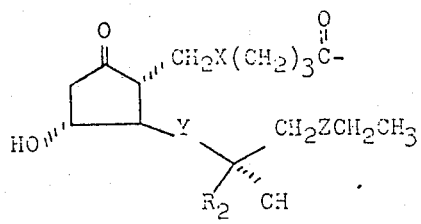

$R_2$ is hydrogen;
X is cis CH=CH;
Y is trans CH=CH; and
Z is $CH_2CH_2$.

7. A compound according to claim 3 of the formula:

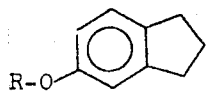

wherein R is

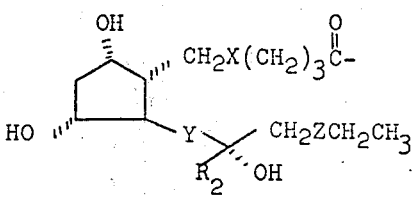

$R_2$ is hydrogen;
X is cis CH=CH;
Y is trans CH=CH; and
Z is $CH_2CH_2$.

* * * * *